(12) United States Patent
Tarekegn

(10) Patent No.: US 11,564,370 B2
(45) Date of Patent: Jan. 31, 2023

(54) HYBRID PEPPER 'E20B30236'

(71) Applicant: Enza Zaden Beheer B.V., Enkhuizen (NL)

(72) Inventor: Yayeh Zewdie Tarekegn, Lakewood Ranch, FL (US)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 17/193,479

(22) Filed: Mar. 5, 2021

(65) Prior Publication Data

US 2021/0282356 A1    Sep. 16, 2021

Related U.S. Application Data

(60) Provisional application No. 62/988,068, filed on Mar. 11, 2020.

(51) Int. Cl.
*A01H 1/00* (2006.01)
*A01H 5/08* (2018.01)
*A01H 6/82* (2018.01)

(52) U.S. Cl.
CPC ............. *A01H 6/822* (2018.05); *A01H 1/00* (2013.01); *A01H 5/08* (2013.01)

(58) Field of Classification Search
None
See application file for complete search history.

(56) References Cited

U.S. PATENT DOCUMENTS

| | | | |
|---|---|---|---|
| 5,262,316 A | 11/1993 | Engler et al. | |
| 5,523,520 A | 6/1996 | Hunsperger et al. | |
| 5,777,196 A | 7/1998 | Hall | |
| 5,948,957 A | 9/1999 | Chapko et al. | |
| 5,959,185 A | 9/1999 | Streit et al. | |
| 5,959,186 A | 9/1999 | Arevalos et al. | |
| 5,969,212 A | 10/1999 | Getschman | |
| 5,973,234 A | 10/1999 | Mueller et al. | |
| 5,977,445 A | 11/1999 | Soper et al. | |
| 6,124,528 A | 9/2000 | Shewmaker | |
| 6,498,287 B2 | 12/2002 | Nash | |
| 7,642,423 B2 | 1/2010 | Nicolet et al. | |
| 8,022,278 B2 | 9/2011 | Lindeman et al. | |
| 8,026,424 B2 | 9/2011 | Van Der Heiden | |
| 8,044,273 B2 | 10/2011 | Van Der Heiden | |
| 8,067,681 B2 | 11/2011 | Van Der Heiden | |
| 8,338,672 B2 | 12/2012 | Lindeman | |
| 8,415,536 B2 | 4/2013 | Leij | |
| 8,536,419 B2 | 9/2013 | Lindeman | |
| 8,618,370 B2 | 12/2013 | Lindeman et al. | |
| 8,816,170 B2 | 8/2014 | Aardse et al. | |
| 9,024,139 B2 | 5/2015 | Della Rocca et al. | |
| 9,089,099 B2 | 7/2015 | Sances Lopez | |
| 9,192,113 B2 | 11/2015 | Lindeman | |
| 9,301,464 B2 | 4/2016 | Sances Lopez | |
| 9,320,215 B2 | 4/2016 | Lindeman et al. | |
| 9,474,220 B2 | 10/2016 | Van Der Heiden | |
| 9,572,313 B2 | 2/2017 | Sances Lopez | |
| PP28,123 P3 | 6/2017 | Lindeman et al. | |
| 9,832,946 B2 | 12/2017 | Tarekegn | |
| 10,051,829 B2 | 8/2018 | Lindeman | |
| PP29,897 P3 | 11/2018 | Lindeman et al. | |
| PP30,957 P3 | 10/2019 | Lindeman | |
| PP30,958 P3 | 10/2019 | Lindeman | |
| 10,492,394 B2 | 12/2019 | Lindeman et al. | |
| 10,595,496 B2 | 3/2020 | Lindeman | |
| 10,595,497 B2 | 3/2020 | Tarekegn | |
| 10,757,903 B2 | 9/2020 | Lindeman | |
| 10,858,667 B2 | 12/2020 | Eckard et al. | |
| 11,185,047 B2 | 11/2021 | Lindeman | |
| 2006/0059585 A1 | 3/2006 | Jankowski et al. | |
| 2006/0195921 A1 | 8/2006 | Van Der Heiden | |
| 2009/0019561 A1 | 1/2009 | Van Der Heiden | |
| 2009/0019599 A1 | 1/2009 | Van Der Heiden | |
| 2009/0019600 A1 | 1/2009 | Van Der Heiden | |
| 2009/0313713 A1 | 12/2009 | Lindeman et al. | |
| 2011/0197313 A1 | 8/2011 | Lindeman et al. | |
| 2012/0066797 A1 | 3/2012 | Lindeman et al. | |
| 2013/0024962 A1 | 1/2013 | Aardse | |
| 2014/0223611 A1 | 8/2014 | Lindeman et al. | |
| 2014/0230084 A1 | 8/2014 | Sances Lopez | |
| 2014/0259195 A1 | 9/2014 | Lindeman | |
| 2014/0283167 A1 | 9/2014 | Sances Lopez | |
| 2014/0289885 A1 | 9/2014 | Van Der Heiden | |
| 2015/0128320 P1 | 5/2015 | Lindeman | |
| 2015/0257352 A1 | 9/2015 | Cook et al. | |
| 2015/0264877 A1 | 9/2015 | Sances Lopez | |
| 2015/0327458 A1 | 11/2015 | Bouw | |

(Continued)

FOREIGN PATENT DOCUMENTS

WO    WO-2001062075 A2    8/2001

OTHER PUBLICATIONS

"Database WPI, Section Ch, Week 20327," Derwent Publications Ltd., Antal, J., 'Kurtovszka Kapia' Capsicum annum, Jan. 28, 2003, 1 page.
Bonnie Plants, (2006). "Carmen Italian Sweet Pepper," downloaded from Bonnie Plants website, 1 page.
Dave's Garden, (2013). "Pepper Capsicum Annum 'Marconi Red'," downloaded from davesgarden.com, 1 page.
Enza Zaden USA, Inc. 'Regulator'. Products & Services. Available online at <https://www.enzazaden.com/us/products-and-services/our-products/Pepper/Regulator>, Obtained on Feb. 2, 2021, 1 page.
Eshed, et al., (1996). "Less-Than-Additive Epistatic Interactions of Quantitative Trait Loci in Tomato Genetics," vol. 143, pp. 1807-1817.

(Continued)

*Primary Examiner* — Phuong T Bui
(74) *Attorney, Agent, or Firm* — Morrison & Foerster LLP

(57) ABSTRACT

A hybrid pepper designated 'E20B30236' is disclosed. The invention relates to the seeds of hybrid pepper 'E20B30236', to the plants of hybrid pepper 'E20B30236', to methods for producing hybrid plants, and to methods for producing other pepper lines, cultivars or hybrids derived from the hybrid pepper 'E20B30236'.

12 Claims, 2 Drawing Sheets
(2 of 2 Drawing Sheet(s) Filed in Color)

(56) References Cited

U.S. PATENT DOCUMENTS

| | | |
|---|---|---|
| 2016/0302371 A1 | 10/2016 | Tarekegn |
| 2017/0196179 A1 | 7/2017 | Lindeman et al. |
| 2017/0223915 A1 | 8/2017 | Lindeman et al. |
| 2018/0035590 P1 | 2/2018 | Lindeman et al. |
| 2018/0042153 P1 | 2/2018 | Lindeman |
| 2018/0042195 A1 | 2/2018 | Lindeman |
| 2018/0049385 A1 | 2/2018 | Tarekegn |
| 2019/0110386 P1 | 4/2019 | Lindeman |
| 2019/0166787 A1 | 6/2019 | Lindeman |
| 2020/0093085 A1 | 3/2020 | Lindeman et al. |
| 2020/0383294 A1 | 12/2020 | Lindeman |
| 2021/0102219 A1 | 4/2021 | Eckard et al. |

OTHER PUBLICATIONS

Honma, S. Capsicum annuum named Migold, PI 586678 deposited 1986, 4 pages.

Jenkins, Merle T., (1940). "The Segregation of Genes Affecting Yield of Grain in Maize," Journal of the American Society of Agronomy, vol. 32, pp. 55-63.

Kingdom of the Netherlands Council for Plant Varieties, 2019. "Official Gazette Nov. 2019," Available online at <https://zoek.officielebekendmakingen.nl/stcrt-2019-62588.pdf>, 13 pages.

Kraft, et al., (2000). "Linkage disequilibrium and fingerprinting in sugar beet," Theor. Appl. Genet., vol. 101, pp. 323-326.

Lefebvre, et al., (1998). "The Capsanthin-Capsorubin Synthase Gene: A Candidate Gene for the y Locus Controlling the Red Fruit Colour in Pepper," Plant Molecular Biology, vol. 36, pp. 785-789.

Newman, et al., (1989). "Synthesis of Two Chromoplast-Specific Proteins During Fruit Development in Capsicum annuum," Plant Physiology, vol. 91, pp. 455-458.

Oren-Shamir, et al., (1993). "Occurrence of the chromoplast protein ChrA correlates with a fruit-color gene in Capsicum annum," Plant Molecular Biology, vol. 21, pp. 549-554.

Osuna-Garcia, et al., (1998). "Endogenous Levels of Tocopherols and Ascorbic Acid during Fruit Ripening of New Mexican-Type Chile (*Capsicum annuum* L.)," Cultivars Journal of Agricultural and Food Chemistry, vol. 46, No. 12, pp. 5093-5096.

Park, et al., (1989). "Susceptibilization of Red Pepper *Capsicum-Annuum* L. to Colletotrichum-Gloeosporioides Penz. in Relation to The Ripening of Fruits," Korean Journal of Plant Pathology, vol. 5, No. 3, pp. 262-270, 2 pages. Abstract Only.

Poehlman, et al., (1995). "Methods in Plant Breeding," Breeding Field Crops, 4th ed., Iowa State University Press, pp. 172-174, 8 pages.

Shifriss, et al., (1992). "Studies of the Inheritance of Mature Fruit Color in *Capsicum annuum* L.," Euphytica, vol. 60, pp. 123-126.

Simpson, et al., (1977). "Chromoplast Ultrastructure of Capsicum Carotenoid Mutants II. Effect of Light and CPTA," Z. Pflanzenphysiol., vol. 83, pp. 309-325.

Smith, Paul G., (1950). "Inheritance of Brown and Green Mature Fruit Color in Peppers," Journal of Heredity, vol. 41, No. 5, pp. 138-140.

Yeam, et al., (2005). "Allele-specific CAPS Markers based on Point Mutations in Resistance Alleles at the pvr1 Locus Encoding eIF4E in Capsicum", Theoretical and Applied Genetics, vol. 112, pp. 178-186.

U.S. Appl. No. 17/745,687, filed May 16, 2022, titled "Hybrid Pepper 'E20B30329'," inventor name "Tarekegn, Yayeh Zewdie," (Copy not submitted herewith pursuant to the waiver of 37 C.F.R. § 1.98(a)(2)(iii)).

HYBRID PEPPER 'E20B30236'

CROSS-REFERENCE TO RELATED APPLICATION

This application claims the benefit of U.S. Provisional Application No. 62/988,068, filed Mar. 11, 2020, which is hereby incorporated by reference in its entirety.

FIELD OF THE INVENTION

The present invention relates to the field of plant breeding. In particular, the present invention relates to a new and distinctive pepper (*Capsicum annuum*) hybrid designated 'E20B30236'.

BACKGROUND OF THE INVENTION

The bell pepper (*Capsicum annuum*) originated in Mexico and the neighboring areas of Central America. Today, pepper plants can be found growing wild in tropical areas around the world. Soon after Columbus's discovery of this plant, it was grown worldwide and used as a spice and a medicine. Pepper is grown as a crop in many countries; hot peppers are generally grown in Latin America and China, while the United States prefers bell peppers. Peppers are used for both fresh consumption, and for processing into powders, sauces, and salsas. Many of the new cultivars grown today can be traced back to the early plants.

The genus *Capsicum* and species *annuum* includes most of the peppers grown in the United States. These can be further grouped into two broad categories: chile peppers which are pungent (hot) and sweet peppers which are non-pungent (mild). The United States produces four percent of the world's *Capsicum* peppers (chile peppers and sweet peppers), ranking sixth behind China, Mexico, Turkey, Spain and Nigeria. Bell peppers are the most common sweet pepper and are found in virtually every retail produce department. While peppers are grown commercially in most states, the U.S. pepper industry is largely concentrated in California and Florida, which together accounted for 78% of output in 2000. New Jersey, Georgia, and North Carolina round out the top five producing states (Economic Research Service, USDA, Vegetables and Melons Outlook/VGS-288/ Dec. 14, 2001).

Bell peppers are eaten raw, cooked, immature and mature. Often nutritional content is altered by the changes in the way they are consumed. Bell peppers are an excellent source of Vitamin C, Vitamin A, and Calcium. Mature red peppers have more of these qualities than the immature green peppers.

Peppers grown in temperate regions are herbaceous annuals, but are herbaceous perennials in regions where temperatures do not drop below freezing. Pepper plants' growth habit may be prostrate, compact, or erect, but it is determinate in that after it produces nine to eleven leaves a single stem terminates in flowers. These flowers then become the edible fleshy fruit for which these plants are grown. For fruit to set, the ovaries need to be fertilized. Auxin is then produced by the seeds, which determine fruit cell elongation. The number of seeds fertilized determines the size and shape of the fruit. The seeds develop on the interior and attach to the veins, and fully developed seed is kidney shaped. Pepper fruits are non-climacteric, which means they do not produce ethylene and need to stay on the vine to continue the ripening process. A deep taproot will form if the plant root system is uninjured during transplanting. The spindle root will develop fibrous secondary root systems spreading laterally and downward. On the soil surface the stem will produce adventitious roots, but not as easily as tomatoes. The leaves of the pepper plant arise singly and are simple, entire, and asymmetrical. Typical of all solanaceous plants, the leaves are arranged alternately on the stem. They are shiny and glabrous and vary in shape from broadly ovate to ovate lanceolate. The flowers develop singly or in twos or threes continuously as the upper structure of the plant proliferates. The corolla is white and five lobed while the anthers are bluish or yellowish in color. The flowers have an open anther formation and will indefinitely self-pollinate. They are also pollinated by insects, which increases the chances of cross-pollination. Unlike tomatoes, whose pollen becomes nonviable in high temperatures, the pepper flowers' pollen is not extremely heat sensitive and it remains viable up to 100° Fahrenheit, allowing fruit to be produced fruit throughout the growing season.

The fruit of a pepper plant is classified as a berry with colors including green, yellow, red, purple, black, brown, white, and orange. Pepper fruit developmental stages are characterized by their colors. Green is the color of an immature fruit, yet green peppers are commonly eaten, and as the fruit matures it changes color. In most commercial cultivars, the color changes are from green to red, green to yellow, or green to orange. In contrast to other pepper varieties, fruits of the purple and white varieties already have these colors as they develop, and therefore do not have a green stage.

Pepper is an important and valuable field crop. Thus, there is a continued need for new hybrid peppers that are appealing to consumers and agronomically sound.

SUMMARY OF THE INVENTION

In order to meet these needs, the present invention is directed to improved hybrid peppers. In one embodiment, the present invention is directed to a hybrid pepper, *Capsicum annuum*, seed designated as 'E20B30236' having NCIMB Accession Number X1. In one embodiment, the present invention is directed to a pepper plant and parts isolated therefrom produced by growing 'E20B30236' pepper seed. In another embodiment, the present invention is directed to a pepper plant and parts isolated therefrom having all the physiological and morphological characteristics of a pepper plant produced by growing 'E20B30236' pepper seed having NCIMB Accession Number X1. In still another embodiment, the present invention is directed to an $F_1$ hybrid pepper seed, plants grown from the seed, and fruit isolated therefrom having 'E20B30236' as a parent, where 'E20B30236' is grown from 'E20B30236' pepper seed having NCIMB Accession Number X1.

Pepper plant parts include pepper leaves, ovules, pollen, seeds, pepper fruits, parts of pepper fruits, flowers, cells, and the like. In another embodiment, the present invention is further directed to pepper leaves, ovules, pollen, seeds, pepper fruits, parts of pepper fruits, and/or flowers isolated from 'E20B30236' pepper plants. In certain embodiments, the present invention is further directed to pollen or ovules isolated from 'E20B30236' pepper plants. In another embodiment, the present invention is further directed to protoplasts produced from 'E20B30236' pepper plants. In another embodiment, the present invention is further directed to tissue culture of 'E20B30236' pepper plants, and to pepper plants regenerated from the tissue culture, where the plant has all of the morphological and physiological characteristics of 'E20B30236' pepper. In certain embodiments, tissue culture of 'E20B30236' pepper plants is produced from a plant part selected from leaf, anther, pistil, stem, petiole, root, root tip, fruit, seed, flower, cotyledon, hypocotyl, embryo and meristematic cell.

In yet another embodiment, the present invention is further directed to a method of selecting pepper plants, by (a) growing 'E20B30236' pepper plants where the 'E20B30236' plants are grown from pepper seed having NCIMB Accession Number X1 and (b) selecting a plant from step (a). In another embodiment, the present invention is further directed to pepper plants, plant parts and seeds produced by the pepper plants where the pepper plants are isolated by the selection method of the invention.

In another embodiment, the present invention is further directed to a method of making pepper seeds by crossing a pepper plant grown from 'E20B30236' pepper seed having NCIMB Accession Number X1 with another pepper plant, and harvesting seed therefrom. In still another embodiment, the present invention is further directed to pepper plants, pepper parts from the pepper plants, and seeds produced therefrom where the pepper plant is grown from seed produced by the method of making pepper seed of the invention.

In another embodiment, the present invention is further directed to a method of making pepper variety 'E20B30236' by selecting seeds from the cross of one 'E20B30236' plant with another 'E20B30236' plant, a sample of 'E20B30236' pepper seed having been deposited under NCIMB Accession Number X1.

According to the invention, there is provided a hybrid pepper plant designated 'E20B30236'. This invention thus relates to the seeds of hybrid pepper 'E20B30236', to the plants of pepper 'E20B30236' and to methods for producing a pepper plant produced by crossing hybrid pepper 'E20B30236' with itself or another pepper plant. This invention also relates to methods for producing other pepper cultivars or hybrids derived from hybrid pepper 'E20B30236' and to the pepper cultivars and hybrids derived by the use of those methods. This invention further relates to pepper seeds and plants produced by crossing hybrid pepper 'E20B30236' with another pepper cultivar.

In another embodiment, the present invention is directed to single gene converted plants of hybrid pepper 'E20B30236'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality.

In another embodiment, the present invention is directed to methods for developing pepper plants in a pepper plant breeding program using plant breeding techniques including recurrent selection, backcrossing, pedigree breeding, restriction fragment length polymorphism enhanced selection, and genetic marker enhanced selection. Seeds, pepper plants, and parts thereof produced by such breeding methods are also part of the invention.

In addition to the exemplary aspects and embodiments described above, further aspects and embodiments will become apparent by reference by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION OF THE INVENTION

Figure 1:
FIG. 1 shows leaves and mature-green fruit of hybrid pepper 'E20B30236'.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits and through selection varieties or parent lines are developed. The goal is to combine in a single variety or hybrid an improved combination of desirable traits from the parental germplasm. These important traits may include higher yield, field performance, fruit and agronomic quality such as fruit shape and length, resistance to diseases and insects, and tolerance to drought and heat.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection. These processes, which lead to the final step of marketing and distribution, usually take from five to ten years from the time the first cross or selection is made.

One goal of pepper plant breeding is to develop new, unique and superior pepper cultivars. A breeder can initially select and cross two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial pepper cultivars thus requires the development of pepper parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs—which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into pepper varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development: Theory and Technique*, Walter Fehr (1991), *Agronomy Books*, 1 (lib[dot]dr[dot]iastate[dot]edu/agron_books/1).

The production of double haploids can also be used for the development of homozygous lines in a breeding program. Double haploids are produced by the doubling of a set of chromosomes from a heterozygous plant to produce a completely homozygous individual. For example, see Wan, et al., *Theor. Appl. Genet.*, 77:889-892, 1989.

Additional non-limiting examples of breeding methods that may be used include, without limitation, those found in *Principles of Plant Breeding*, John Wiley and Son, pp. 115-161 (1960); *Principles of Cultivar Development: Theory and Technique*, Walter Fehr (1991), *Agronomy Books*, 1 (lib[dot]dr[dot]iastate[dot]edu/agron_books/1).

Definitions

In the description and tables that follow, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Covered cultivation. Any type of cultivation where the plants are not exposed to direct sunlight. The covering includes but is not limited to greenhouses, glasshouses, net-houses, plastic houses and tunnels.

Essentially all the physiological and morphological characteristics. A plant having essentially all the physiological and morphological characteristics means a plant having the physiological and morphological characteristics of the recurrent parent, except for the characteristics derived from the converted gene.

Internode. An "internode" refers to the stem segment between nodes.

Mature-green. As used herein, "mature-green", "mature-green fruit", "mature-green pepper", "mature-green pepper fruit" refer to pepper fruit that has reached full size and the seeds inside are mature, but the fruit has not yet changed color.

Pepper fruit. As used herein, a "pepper fruit" is a fruit produced by a *Capsicum annuum* plant and is commonly referred to as a bell pepper. The color of a pepper fruit can be green, red, yellow, orange and, more rarely, white, black, and brown, depending on when they are harvested and the specific cultivar. Green peppers are unripe bell peppers, while the others are all ripe, with the color variation based on cultivar selection.

Propagate. To "propagate" a plant means to reproduce the plant by means including, but not limited to, seeds, cuttings, divisions, tissue culture, embryo culture or other in vitro method.

Quantitative Trait Loci (QTL). As used herein, "quantitative trait loci" refers to genetic loci that control to some degree numerically representable traits that are usually continuously distributed.

Regeneration. As used herein, "regeneration" refers to the development of a plant from tissue culture.

Single gene converted. As used herein, "single gene converted" or "conversion plant" refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Overview of the Hybrid Pepper Variety 'E20B30236'

Figure 2:
FIG. 2 shows harvested mature-green fruit of hybrid pepper 'E20B30236'.

Hybrid pepper 'E20B30236' is a bell pepper that produces rectangular fruit having a dark green color when immature and a medium red color when mature (ripe). This variety is suitable for harvesting at mature-green stage. This variety is suitable for cultivation both in the field and in the greenhouse. Hybrid pepper 'E20B30236' is suitable for growing in the fall and spring seasons of the eastern USA and similar agroecological regions. Additionally, hybrid pepper 'E20B30236' is highly resistant to Tobamovirus, Pathotype:0 (Tm:0) and Bacterial Leaf Spot (BLS) (*Xanthomonas euvesicatoria*) races 0-10, and intermediate resistant to Tomato Spotted Wilt Virus (TSWV). FIG. 1 shows leaves and mature-green fruit of hybrid pepper 'E20B30236', and FIG. 2 shows harvested mature-green fruit of hybrid pepper 'E20B30236'. Hybrid pepper 'E20B30236' is the result of numerous generations of plant selections for its two parent lines, and was chosen for its plant size, fruit color, fruit shape, fruit size, and disease resistance.

This variety has shown uniformity and stability for the traits, within the limits of environmental influence for the traits. Hybrid pepper 'E20B30236' has been increased with continued observation for uniformity. No variant traits have been observed or are expected in 'E20B30236'.

Objective Description of Hybrid Pepper 'E20B30236'

Hybrid pepper variety 'E20B30236' has the following morphologic and other characteristics:

Plant:
Habit: Semi-spreading
Attitude: Semi-erect
Growth: Indeterminate
Height: Medium (50-75 cm at first harvest)
Shortened internode: Absent
Leaves:
Mature leaf shape: Ovate
Color: Medium green
Leaf and stem pubescence: Absent
Blistering: Absent
Flowers:
Number of flowers per leaf axil: 1
Anther color: Yellow
Corolla color: White
Self-incompatibility: Absent
Fruit:
Group: Bell
Immature fruit color: Dark green
Mature (ripe) fruit color: Medium red
Pungency: Sweet
Flavor: Moderate pepper flavor
Glossiness: Moderate
Surface texture: Smooth or very slightly wrinkled
Position: Pendent
Calyx shape: Saucer-shaped
Length: 9 cm
Diameter: 10 cm
Average number of fruits per plant: 6 marketable fruits
Base shape: Cupped
Apex shape: Blunt
Shape in longitudinal section: Rectangular
Sinuation of pericarp at basal part: Medium
Sinuation of pericarp excluding basal part: Weak
Average number of locules: Four
Days from transplanting until mature-green stage: 70-75 days
Days from transplanting until mature (ripe) red/orange/yellow stage: 85-90 days
Seed:
Seed color: Yellow
Growth Conditions:
Type of culture: Both field and greenhouse
Principle use: Fresh market
Machine harvest: Not adapted
Anthocyanin Coloration:
Seedling hypocotyl: Absent
Stem: Absent
Node: Absent
Leaf: Absent
Pedicel: Absent
Calyx: Absent
Fruit: Absent Disease/Pest Resistance:
Tobamovirus, Pathotype:0 (Tm:0): Highly resistant
Tomato Spotted Wilt Virus (TSWV) race 0: Intermediate resistant
Bacterial Leaf Spot (BLS) (*Xanthomonas euvesicatoria*) races 0-10: Highly resistant Comparison to Most Similar Variety Table below compares some of the characteristics of hybrid pepper variety 'E20B30236' with similar variety, 'Aristotle' (unpatented). Column 1 lists the characteristics, column 2 shows the characteristics for hybrid pepper variety 'E20B30236', and column 3 shows the characteristics for most similar pepper variety 'Aristotle'.

TABLE

| Characteristic | 'E20B30236' | 'Aristotle' |
| --- | --- | --- |
| Plant height | Medium (50-75 cm at first harvest) | Compact (less than 50 cm at first harvest) |
| Days from transplanting until green mature | 70-75 days (Medium) | Less than 70 days (Early) |
| Resistance to Bacterial leaf spot (BLS) (*Xanthomonas euvesicatoria*) | Resistant to races 0-10 | Resistant to races 1-3 |
| Resistance to Tomato Spotted Wilt Virus (TSWV) | Intermediate resistant to TSWV race 0 | Not resistant |

FURTHER EMBODIMENTS

This invention is also directed to methods for producing a pepper plant by crossing a first parent pepper plant with a second parent pepper plant, wherein the first or second pepper plant is the pepper plant 'E20B30236'. Further, both first and second parent pepper plants may be 'E20B30236'. Therefore, any methods using pepper hybrid 'E20B30236' are part of this invention: selfing, backcrosses, hybrid breeding, and crosses to populations. Any plants produced using pepper hybrid 'E20B30236' as at least one parent are within the scope of this invention.

Gene Conversions

When the terms pepper plant, hybrid, cultivar or pepper line are used in the context of the present invention, this also includes any single gene conversions. The term "single gene converted plant" as used herein refers to those pepper plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term "backcrossing" as used herein refers to the repeated crossing of a hybrid progeny back to one of the parental pepper plants for that line, backcrossing 1, 2, 3, 4, 5, 6, 7, 8, or more times to the recurrent parent. The parental pepper plant which contributes the gene for the desired characteristic is termed the nonrecurrent or donor parent. This terminology refers to the fact that the nonrecurrent parent is used one time in the backcross protocol and therefore does not recur. The parental pepper plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a pepper plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Examples of single gene traits include but are not limited to, male sterility, modified fatty acid metabolism, modified carbohydrate metabolism, herbicide resistance, nematode resistance, resistance for bacterial, fungal, or viral disease, insect resistance, enhanced nutritional quality, industrial usage, and yield enhancement. These genes are generally inherited through the nucleus. Several of these single gene traits are described in U.S. Pat. Nos. 5,777,196, 5,948,957 and 5,969,212, the disclosures of which are specifically hereby incorporated by reference.

Tissue Culture

Further reproduction of the variety can occur by tissue culture and regeneration. Tissue culture of various tissues of pepper and regeneration of plants therefrom is well known and widely published. For example, reference may be had to Teng, et al., *HortScience*. 1992, 27: 9, 1030-1032 Teng, et al., *HortScience*. 1993, 28: 6, 669-1671, Zhang, et al., *Journal of Genetics and Breeding*. 1992, 46: 3, 287-290, Webb, et al., *Plant Cell Tissue and Organ Culture*. 1994, 38: 1, 77-79, Curtis, et al., *Journal of Experimental Botany*. 1994, 45: 279, 1441-1449, Nagata, et al., *Journal for the American Society for Horticultural Science*. 2000, 125: 6, 669-672, and Ibrahim, et al., *Plant Cell, Tissue and Organ Culture*. (1992), 28(2): 139-145. It is clear from the literature that the state of the art is such that these methods of obtaining plants are routinely used and have a very high rate of success. Thus, another aspect of this invention is to provide cells which upon growth and differentiation produce pepper plants having the physiological and morphological characteristics of the hybrid 'E20B30236'.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, and the like. Means for preparing and maintaining plant tissue culture are well known in the art. By way of example, a tissue culture comprising organs has been used to produce regenerated plants. U.S. Pat. Nos. 5,959,185; 5,973,234; and 5,977,445 describe certain techniques, the disclosures of which are incorporated herein by reference.

Additional Breeding Methods

This invention also is directed to methods for producing a pepper plant by crossing a first parent pepper plant with a second parent pepper plant wherein the first or second parent pepper plant is a pepper plant of hybrid 'E20B30236'. Further, both first and second parent pepper plants can come from pepper hybrid 'E20B30236'. Thus, any such methods using pepper hybrid 'E20B30236' are part of this invention: selfing, backcrosses, hybrid production, crosses to populations, and the like. All plants produced using pepper hybrid 'E20B30236' as at least one parent are within the scope of this invention, including those developed from cultivars derived from pepper hybrid 'E20B30236'. Advantageously, this pepper cultivar could be used in crosses with other, different, pepper plants to produce the first generation ($F_1$) pepper hybrid seeds and plants with superior characteristics. The cultivar of the invention can also be used for transformation where exogenous genes are introduced and expressed by the cultivar of the invention. Genetic variants created either through traditional breeding methods using pepper hybrid 'E20B30236' or through transformation of hybrid 'E20B30236' by any of a number of protocols known to those of skill in the art are intended to be within the scope of this invention.

The following describes breeding methods that may be used with pepper hybrid 'E20B30236' in the development of further pepper plants. One such embodiment is a method for developing progeny pepper plants in a pepper plant breeding program comprising: obtaining the pepper plant, or a part thereof, of hybrid 'E20B30236', utilizing said plant or plant part as a source of breeding material, and selecting a pepper hybrid 'E20B30236' progeny plant with molecular markers in common with hybrid 'E20B30236' and/or with morphological and/or physiological characteristics selected from the characteristics listed above. Breeding steps that may be used in the pepper plant breeding program include pedigree breeding, backcrossing, mutation breeding, and recurrent selection. In conjunction with these steps, techniques such as RFLP-enhanced selection, genetic marker enhanced selection (for example, SSR markers) and the making of double haploids may be utilized.

Another method involves producing a population of pepper hybrid 'E20B30236' progeny pepper plants, by crossing hybrid 'E20B30236' with another pepper plant, thereby producing a population of pepper plants, which, on average, derive 50% of their alleles from pepper hybrid 'E20B30236'. A plant of this population may be selected and repeatedly selfed or sibbed with a pepper plant resulting from these successive filial generations. One embodiment of this invention is the pepper cultivar produced by this method and that has obtained at least 50% of its alleles from pepper hybrid 'E20B30236'.

Additional methods include, without limitation, chasing selfs. Chasing selfs involves identifying inbred plants among pepper plants that have been grown from hybrid pepper seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present invention relates a method for producing an inbred pepper variety by: planting seed of the pepper variety 'E20B30236'; growing plants from the seed; identifying one or more inbred pepper plants; controlling pollination in a manner which preserves homozygosity of the one or more inbred plants; and harvesting resultant seed from the one or more inbred plants. The step of identifying the one or more inbred pepper plants may further include identifying plants with decreased vigor, i.e., plants that appear less robust than plants of the pepper variety 'E20B30236'. Pepper plants capable of expressing substantially all of the physiological and morphological characteristics of the parental inbred lines of pepper variety 'E20B30236' include pepper plants obtained by chasing selfs from seed of pepper variety 'E20B30236'.

One of ordinary skill in the art will recognize that once a breeder has obtained inbred pepper plants by chasing selfs from seed of pepper variety 'E20B30236', the breeder can then produce new inbred plants such as by sib-pollinating, or by crossing one of the identified inbred pepper plant with a plant of the pepper variety 'E20B30236'.

One of ordinary skill in the art of plant breeding would know how to evaluate the traits of two plant varieties to determine if there is no significant difference between the two traits expressed by those varieties. For example, see Fehr and Walt, *Principles of Cultivar Development*, pp. 261-286 (1987). Thus the invention includes pepper hybrid 'E20B30236' progeny pepper plants comprising a combination of at least two hybrid 'E20B30236' traits selected from the group consisting of those listed above or the hybrid 'E20B30236' combination of traits listed in the Summary of the Invention, so that said progeny pepper plant is not significantly different for said traits than pepper hybrid 'E20B30236' as determined at the 5% significance level when grown in the same environmental conditions. Using techniques described herein, molecular markers may be used to identify said progeny plant as a pepper hybrid 'E20B30236' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of pepper hybrid 'E20B30236' may also be characterized through their filial relationship with pepper hybrid 'E20B30236', as for example, being within a certain number of breeding crosses of pepper hybrid 'E20B30236'. A breeding cross is a cross made to introduce new genetics into the progeny, and is distinguished from a cross, such as a self or a sib cross, made to select among existing genetic alleles. The lower the number of breeding crosses in the pedigree, the closer the relationship between pepper hybrid 'E20B30236' and its progeny. For example, progeny produced by the methods described herein may be within 1, 2, 3, 4, or 5 breeding crosses of pepper hybrid 'E20B30236'.

As used herein, the term "plant" includes plant cells, plant protoplasts, plant cell tissue cultures from which pepper plants can be regenerated, plant calli, plant clumps and plant cells that are intact in plants or parts of plants, such as fruit, leaves, pollen, embryos, cotyledons, hypocotyl, roots, root tips, anthers, pistils, flowers, seeds, stems and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the hybrid pepper 'E20B30236' is maintained by Enza Zaden USA, Inc., having an address at 7. Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 625 seeds of hybrid pepper 'E20B30236' were deposited on DATE according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number X1. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. A hybrid pepper seed designated as 'E20B30236', representative sample of seed having been deposited under NCIMB Accession Number 43756.

2. A pepper plant produced by growing the seed of claim 1.

3. A plant part from the plant of claim 2, wherein said part is a leaf, a fruit, or a cell.

4. The plant part of claim 3, wherein said part is a fruit.

5. A pepper plant having all the physiological and morphological characteristics of the pepper plant of claim 2.

6. A plant part from the plant of claim 5, wherein said part is a leaf, a fruit, or a cell.

7. The plant part of claim 6, wherein said part is a fruit.

8. Pollen or an ovule of the plant of claim 2.

9. A protoplast produced from the plant of claim 2.

10. A tissue culture produced from protoplasts or cells from the plant of claim 2, wherein said cells or protoplasts are produced from a plant part selected from the group consisting of leaf, anther, pistil, stem, petiole, root, root tip, fruit, flower, cotyledon, hypocotyl, and meristematic cell.

11. A pepper plant regenerated from the tissue culture of claim 10, wherein the plant has all of the morphological and physiological characteristics of a pepper plant produced by growing hybrid pepper seed designated as 'E20B30236', representative sample of seed having been deposited under NCIMB Accession Number 43756.

12. A method of making pepper seeds, said method comprising crossing the plant of claim 2 with another pepper plant and harvesting seeds therefrom.

* * * * *